United States Patent
Fothergill et al.

(10) Patent No.: US 10,000,776 B2
(45) Date of Patent: Jun. 19, 2018

(54) GAS PHASE BIOCATALYSIS METHOD AND PROCESS

(71) Applicant: Michael David Fothergill, Nelson, Lancashire (GB)

(72) Inventors: Michael David Fothergill, Nelson (GB); Timothy Gibson, Wakefield (GB); Gerard Garcia Sobany, Ottnang am Hausruck (AT)

(73) Assignee: Michael David Fothergill, Nelson, Lancashire (GB)

( * ) Notice: Subject to any disclaimer, the term of this patent is extended or adjusted under 35 U.S.C. 154(b) by 0 days. days.

(21) Appl. No.: 14/433,014

(22) PCT Filed: Oct. 10, 2013

(86) PCT No.: PCT/GB2013/052647
§ 371 (c)(1),
(2) Date: Apr. 1, 2015

(87) PCT Pub. No.: WO2014/057277
PCT Pub. Date: Apr. 17, 2014

(65) Prior Publication Data
US 2015/0232887 A1 Aug. 20, 2015

(30) Foreign Application Priority Data
Oct. 10, 2012 (GB) .................................. 1218186.3

(51) Int. Cl.
*C12P 7/04* (2006.01)
*C12N 11/14* (2006.01)
*C12N 11/18* (2006.01)

(52) U.S. Cl.
CPC .............. *C12P 7/04* (2013.01); *C12N 11/14* (2013.01); *C12N 11/18* (2013.01)

(58) Field of Classification Search
None
See application file for complete search history.

(56) References Cited

U.S. PATENT DOCUMENTS

| | | | |
|---|---|---|---|
| 5,200,334 A | 4/1993 | Dunn et al. | |
| 5,670,332 A | 9/1997 | Kuhl et al. | |
| 6,143,556 A | 11/2000 | Trachtenberg | |
| 6,440,711 B1 | 8/2002 | Davé | |
| 2005/0266290 A1* | 12/2005 | Sun | B82Y 5/00 429/401 |
| 2007/0042479 A1* | 2/2007 | Dave | C12P 7/04 435/157 |
| 2011/0200889 A1* | 8/2011 | Kumita | H01M 8/16 429/401 |

FOREIGN PATENT DOCUMENTS

WO 2011/163323 12/2011

OTHER PUBLICATIONS

Cameron, Paula A. et al., "Direct transesterification of gases by 'dry' immobilized lipase," Biotechnology and Bioengineering, vol. 78, No. 3 pp. 251-254, May 5, 2002.
Dravis, Bryan C. et al., "Enzymatic dehalogenation of gas phase substrates with haloalkane dehalogenase," Biotechnology and Bioengineering, vol. 69, No. 3, Aug. 5, 2000.
Ferloni, Clara et al., "Optimization of enzymatic gas-phase reactions by increasing the long-term stability of the catalyst," Biotechnol. Prog. 2004, 20, 975-978.
Dave, Bakul C. et al., "Prospects for Methanol Production," Bioenergy, ASM Press, Washington, US Jan. 1, 2008, pp. 235-245.
Debeche, Takoua et al., "Structured fiber supports for gas phase biocatalysis," Enzyme and Microbial Technology 36 (2005) 911-916.
Russell, Alan J. et al., "Catalyze gas-phase reactions with enzymes," Chemtech, Oct. 1996, pp. 24-27.
Demir, Ayhan S. et al., "Selective oxidation and reduction reactions with cofactor regeneration mediated by galactitol-, lactate-, and formate dehydrogenases immobilized on magnetic nanoparticles," Journal of Biotechnology 152 (2011) 176-183.
Jeromin, Günter E., "Superabsorbed alcohol dehydrogenase—a new catalyst for asymmetric reductions," Biotechnol Lett (2009) 31:1717-1721.
Mak, Karen K.W. et al., "An amperometric bi-enzyme sensor for determination of formate using cofactor regeneration," Biosensors and Bioelectronics 18 (2003) 1095-1100.
Trivedi, Archana et al., "Optimization of adsorptive immobilization of alcohol dehydrogenases," Journal of Bioscience and Bioengineering vol. 99, No. 4, 340-347, 2005.
Vianello, Fabio et al., "On-line detection of atmospheric formaldehyde by a conductometric biosensor," Biosensors and Bioelectronics 22 (2007) 920-925.
Silverman, Josh et al., "High Mass Transfer Bioreators for Methane Fermentation" (Feb. 24, 2014), http://calysta.com/pdfs/arpae-innovation-summit-2014-calysta-poster.pdf.
Turney, Damon et al., "Achieve Mass-Transfer Requirements in Methane Gas-to Liquid Bioreactors", (Nov. 10, 2015), 2015 AIChE Annual Meeting, Nov. 8-15, 2015, Salt Lake City, UT, (Abstract Only), https://aiche.confex.com/aiche/2015/webprogram/Paper439717.html.
www.methanotroph.org/wiki/performance-and-yield, Methanotroph Commons, (Sep. 17, 2013).

* cited by examiner

*Primary Examiner* — Michelle F. Paguio Frising
(74) *Attorney, Agent, or Firm* — Weaver Austin Villeneuve & Sampson, LLC.

(57) ABSTRACT

A method of enzyme conversion comprises the steps of immobilising an enzyme composition on a support material; drying the support material and enzyme composition to form a solid phase immobilised enzyme system; contacting the system with one or more reagents in the gas phase; allowing the enzyme system to convert the reagent(s) to product(s); wherein the enzyme composition may comprise a single enzyme or a first enzyme plus a second enzyme or multiple enzymes; and a co-factor which may be converted between first and second states; wherein the co-factor in the first state promotes reaction of the first enzyme; and wherein the co-factor in the second state promotes reaction of the second enzyme; or wherein the co-factor oscillates between first and second states with multiple enzymes.

15 Claims, 5 Drawing Sheets

Reaction Sequence

Alcohol Dehydrogenase Biocatalysis

Methanol Calibration Plot.

Dry Phase Methanol Detection Device.

GC of Acetone Conversion to Isopropanol and Prenol to Prenal.

Formic Acid from Methanol

Alkene Mono-oxygenase Reaction Sequence

Propylene oxide calibration plot

GAS PHASE BIOCATALYSIS METHOD AND PROCESS

This invention relates to a method of enzymic conversion in which an enzyme composition is mobilised on a solid substrate for reaction with a gaseous reagent. The invention also relates to an enzymic conversion system for use in the method.

A number of processes describing biocatalytic reactions in gas phase applications have been described. However they have different requirements which make them partially 'gas phase' systems. U.S. Pat. No. 5,670,332 (Kuhl et al, Degussa) discloses solid phase systems operating by gas phase reactants being passed through a mixture of enzyme and solid phase substrates. The system is able to convert the solid phase substrate into a product in the mixture which is subsequently extracted to recover the product. Examples given include peptides generated using proteases such as chymotrypsin.

U.S. Pat. No. 6,440,711 Bakul Davé, Southern University of Illinois) discloses a sol-gel immobilised enzyme system comprising formate dehydrogenase, formaldehyde dehydrogenase and alcohol dehydrogenase configured into the pores of the sol-gel to generate methanol from $CO_2$ and reduced co-factor NADH. In this case liquid water is added and the $CO_2$ is bubbled through the suspension. Photosystem II (PSII) obtained from spinach leaves was added to NADH to enable the continuous production of methanol to occur in solution. The sol-gel system is important to make the enzymes function effectively in the reverse direction. Publications by Kuwabata et al., (1994), Kuwabata et al., 1990 and Mandler et al., (1988) are cited as supporting documentation.

WO2011/163323 discloses a modified carbonic anhydrase enzyme that is immobilised into a reactor and which is used in a process to remove $CO_2$ from an atmosphere. However a first step requires the $CO_2$ to be captured into a liquid medium, e.g. water. The water/$CO_2$ mixture is then passed over the immobilised modified enzyme to give bicarbonate ions which are then removed by a metal precipitation step using calcium ions. This results in overall removal of $CO_2$ from the atmosphere. This is the basis of a commercial process by $CO_2$ Solutions Inc. However the use of water as a solvent for $CO_2$ will introduce mass transfer barriers in the process. Also the $CO_2$ ends up as a solid precipitate of calcium carbonate and not a useful fine chemical such as formic acid.

SUMMARY

According to a first aspect of the present invention, a method of enzymic conversion comprises the steps of:
immobilising an enzyme composition on a support material;
drying the support material and enzyme composition to form a solid phase immobilised enzyme system;
contacting the system with a gaseous reagent; and
allowing the enzyme system to convert the reagent to a product;
wherein the enzyme composition comprises a first enzyme, a second enzyme and a co-factor which may be converted between first and second states;
wherein the co-factor in the first state promotes reaction of the first enzyme; and
wherein the co-factor in the second state promotes reaction of the second enzyme.

According to a second aspect of the present invention, an enzymic conversion system comprises:
a dried enzyme composition on a support material comprising a first enzyme, a second enzyme and a co-factor which may be converted between first and second states;
wherein the co-factor in the first state promotes reaction of the first enzyme; and
wherein the co-factor in the second state promotes reaction of the second enzyme.

The first and second states of the co-factor may be oxidized or reduced states. A preferred co-factor is NAD/NADH.

The enzyme is preferably dried to a sufficient extent to produce an immobilised enzyme system. However, the enzyme is preferably not dried to such a low water level that it is deactivated. A water content of 0.05% to 5% w/v may be employed.

Use of the method of the present invention allows complex multi-subunit enzymes to operate catalytically in gas phase systems.

The support may be an inorganic substrate, for example sand, silica or glass. The support material may be provided in the form of particles or beads. Preferably, porous beads are employed. These may have a high internal surface area.

The system may comprise a fluidised bed in which the particulate support material is fluidised by passage of the gaseous reagent.

The first enzyme may be selected from the group consisting of methane mono-oxygenase (MMO) and alkene mono-oxygenase (AMO) or any other mono-oxygenase.

The second enzyme may be selected from one or more dehydrogenase enzymes, for example:
alcohol dehydrogenase;
formaldehyde dehydrogenase; or
formate dehydrogenase.

In preferred embodiments of the invention, liquid water is absent from the enzyme composition, reagent and the support.

In preferred embodiments, the enzymes are dried on the support. Immobilisation of the enzyme within a sol or gel is not preferred.

Use of a silica or other solid substrate supported enzyme system is advantageous to improve the mass transfer properties of the process, as water is not used. Diffusion processes are much faster in the gas phase than in the liquid phase, leading to higher rates of reaction.

Furthermore, use of a gas phase system confers a considerable increase in operating longevity or thermostability of the enzymes employed.

Use of a system including MMO as an enzyme component provides a method for conversion of methane using molecular oxygen to form methanol. This provides a process for production of methanol using the cheap substrates methane and oxygen.

In a multi-enzyme system, alcohol dehydrogenase (ADH), formaldehyde dehydrogenase (FADH) and formate dehydrogenase (FODH) may be immobilised on a solid support to produce formic acid from methanol in a gas phase reaction.

In a further multi-enzyme system, methane mono-oxygenase (MMO), alcohol dehydrogenase (ADH), formaldehyde dehydrogenase (FADH) and formate dehydrogenase (FODH) may be immobilised on a support to produce formic acid from methane, oxygen and carbon-dioxide. The enzymes may be immobilised as a mixture or may be located on individual support regions of the supports.

Use of the enzyme alkene mono-oxygenase allows the conversion of an alkene such as propylene to a chiral product such as R-propylene oxide. The enzyme reaction significantly favours the production of one chiral form over the other.

A multi-enzyme system comprising alkene mono-oxygenase (AMO), alcohol dehydrogenase (ADH), formaldehyde dehydrogenase (FADH) and formate dehydrogenase (FODH) may be immobilised on a support in order to produce $CO_2$ and water from methanol and R-propylene oxide from propylene using NADH recycled from NAD via the oxidation of methanol.

The system of this invention may be used as a sensor to detect the reagent in a dry phase test.

Enzymes when immobilised in a low water environment may retain significant biocatalytic activity, provided there is a micro-environment that maintains a certain amount of water around the enzyme structure. The invention disclosed combines production of a stable admix of enzymes and cheap, simple support materials such as porous silica particles, a rapid vacuum assisted drying step at elevated temperature and the demonstration of enzyme biocatalytic activity with purely gaseous and/or vapour phase substrates to generate fine chemical products.

It was unexpected that an extremely complex multi-subunit enzyme, methane mono-oxygenase (MMO), was found to retain biocatalytic activity when immobilised allowing conversion of gaseous methane to methanol using indigenous reduced co-factor NADH and oxygen in the gas phase. Unpurified, crude preparations of MMO may be used to biocatalytically generate methanol from methane. The reduced co-factor NADH may be recycled within a silica supported enzyme mixture, purely with gas phase reactions, i.e. no liquid water added is also an important feature.

BRIEF DESCRIPTION OF THE DRAWINGS

The invention is further described by means of example but not in any limitative sense with reference to the accompanying drawings, of which.

DETAILED DESCRIPTION

Figure 1:
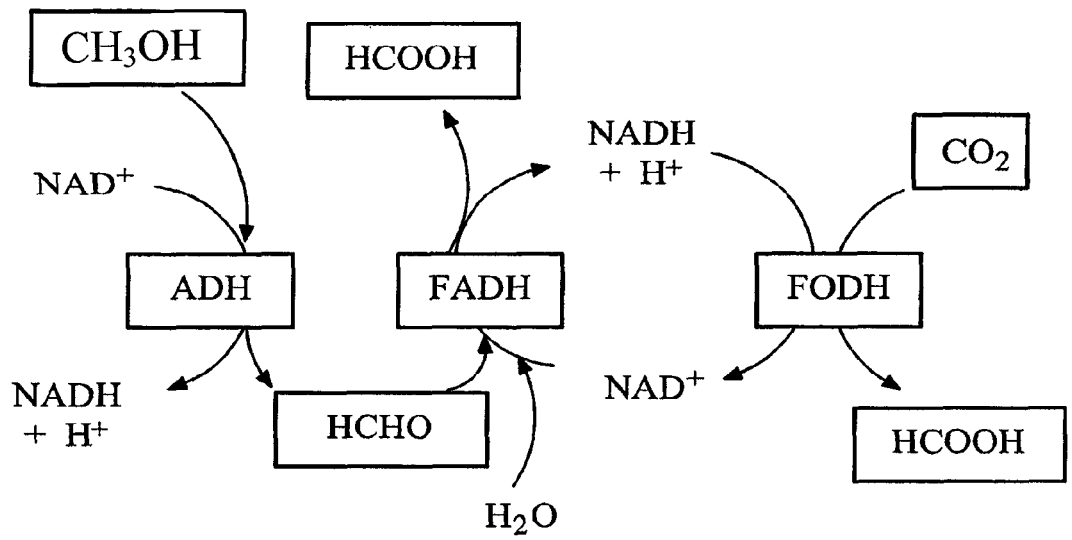
FIG. 1 shows a reaction sequence in accordance with the invention.

To demonstrate the recycling of the NAD/NADH co-factor couple a combination of dehydrogenase enzymes, alcohol dehydrogenase, formaldehyde dehydrogenase and formate dehydrogenase were used in the sequence shown in FIG. 1.

A major advantage of the present process is that an enzymatic conversion may be carried out in the gas phase, with the enzyme supported in a solid dry state on porous beads with a high internal surface area. This form of supported enzyme material is suitable for fluidisation where the reactant(s) in the gas phase lifts the enzyme beads creating a particulate fluid form. The effect of this is to greatly enhance the mass transfer properties of the process and allow much more efficient biocatalysis. No liquid water being present, the access of the substrates to the active sites of the enzymes is not prevented by poor mass transfer.

A second advantage is that substrates that are water insoluble but which have a vapour pressure, i.e. which are volatile can reach the enzymes with minimal issues with the water insolubility. Methane is a good example of this as it is very sparingly soluble in water but it is converted to methanol by the MMO in the gas phase quite efficiently.

Single Enzyme Systems

1) Methane Mono-Oxygenase

A single enzyme that transforms methane using molecular oxygen in the presence of reduced co-factor NADH was tested. Methane mono-oxygenase (MMO) is a multi-subunit enzyme with three distinct components:

a hydroxylase sub-unit that reacts with methane to make methanol;

a reductase sub-unit acts to make NADH and supply the reducing power to the hydroxylase;

protein B acts as a regulation sub-unit and promotes hydroxylase activity.

All 3 sub-units need to be present and active to make MMO work correctly.

One millilitre of crude MMO lysate was used to produce an immobilised MMO preparation. This was tested for activity by blowing a mixture of methane and air and $CO_2$ through an immobilised substrate and the resulting absorbance at a wavelength of 500 nm was measured. See Example 1 below.

2) Alcohol Dehydrogenase

A second single enzyme system based on yeast alcohol dehydrogenase (ADH) was immobilised on silica beads.

Figure 2:
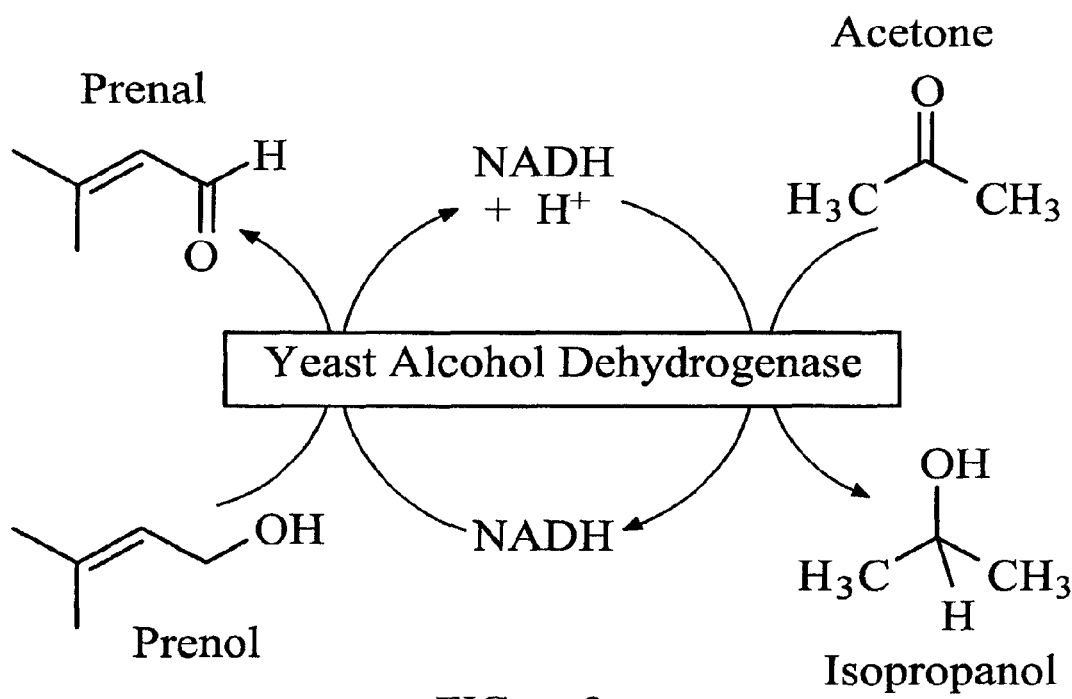
FIG. 2 shows a reaction sequence for alcohol dehydrogenase biocatalysis.

The appearance of prenal and isopropanol in the exhaust gas stream was observed using a gas chromatography method, indicating enzyme activity was occurring according to FIG. 2.

Multienzyme Systems

1) Alcohol dehydrogenase (ADH) formaldehyde dehydrogenase (FADH) and formate dehydrogenase (FODH) were coupled together to produce formic acid from methanol in a gas phase reaction seen in FIG. 1. This reaction sequence was used to generate useful fine chemicals from cheaper precursors and at the same time provide a $CO_2$ sequestration system that would fix the $CO_2$ into an organic fine chemical, suitable for use in chemical synthesis.

The overall reaction sequence was:

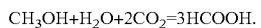
$$CH_3OH+H_2O+2CO_2=3HCOOH.$$

2) A second multienzyme system based on four enzymes was used. Methane mono-oxygenase (MMO), alcohol dehydrogenase (ADH) formaldehyde dehydrogenase (FADH) and formate dehydrogenase (FODH) were coupled together to produce formic acid from methane, oxygen and $CO_2$. The overall reaction performed by the enzyme system was as follows:

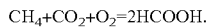
$$CH_4+CO_2+O_2=2HCOOH.$$

In this case various mixtures of the dry enzymes ADH, FADH and FODH were added to 1 ml of sMMO crude lysate together with 1 ml of 50 mM sodium phosphate buffer pH 7.5, dissolved completely and then added to 200 g of silica beads. Dehydration was carried out and the resulting dry powder packed into a 5 cm column. Introduction of methane, air and $CO_2$ resulted in the production of formic acid which was measured quantitatively using a colorimetric formazan assay as before. See Example 4.

3) A third multi-enzyme system based on four enzymes was used. The enzymes alkene mono-oxygenase (AMO), alcohol dehydrogenase (ADH), formaldehyde dehydrogenase (FADH) and formate dehydrogenase (FODH) were coupled together to produce $CO_2$ and water from methanol and R-propylene oxide from propylene.

The reaction catalysed by AMO is as follows:

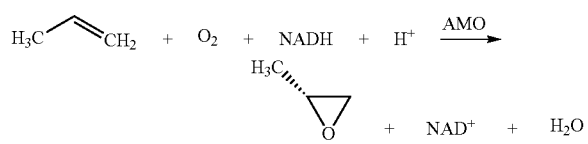

Propylene R-Propylene oxide

The reaction catalysed by the three enzymes used to regenerate the cofactor (ADH, FADH and FODH) is:

$$CH_3OH + 3NAD^+ + H_2O = 3NADH + 3H^+ + CO_2$$

Combining the two reactions yields the net reaction below:

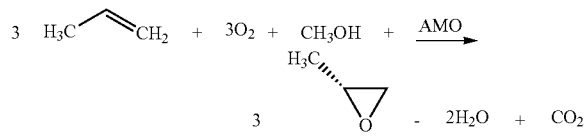

See Example 5.

EXAMPLES

1. Conversion of Methane to Methanol

Methane is fixed by various methylotrophic bacteria and the enzyme that does this is Methane Mono-Oxygenase (MMO). This is a multi-subunit enzyme.

A crude cell lysate produced from a cell paste harvested from the fermentation of the methanotrophic bacteria, *Methylosinus trichosporium* OB3b (Fox et al. J Biol Chem 264 (1969) p 10023-10033) was used to produce the soluble MMO (sMMO).

The crude lysate contained approximately 3 mg per ml of sMMO and to 200 mg of silica beads (SI 1410 grade, Grace Davidson Catalysts), 1 ml of lysate was added. The mixture was dehydrated over a 2 hour period under reduced pressure over a bed of freshly dried silica gel (2-3 kg in weight).

The resulting dry powder was stored at 4° C. until required.

The powder was weighed into a 5 cm length of 6 mm (¼ inch) polyfluoroacetate tubing with porous polystyrene plugs at each end to produce a mini-column reactor that allowed unrestricted gas flow. Typically 150-200 mg powder was used.

The gas flow used was made up of a mixture of methane (4-5 ml per minute, air 10-12 ml per minute and sometimes $CO_2$ was added at 4-5 ml per minute to see if this had any effect on the catalytic rate). Methanol production was measured using a colorimetric reaction based on alcohol oxidase, horseradish peroxidase and colour reagents 4-aminoantipyrine and N,N'-bis hydroxyethyl aniline, which gives a purple imino dye on reaction with methanol.

Figure 3:
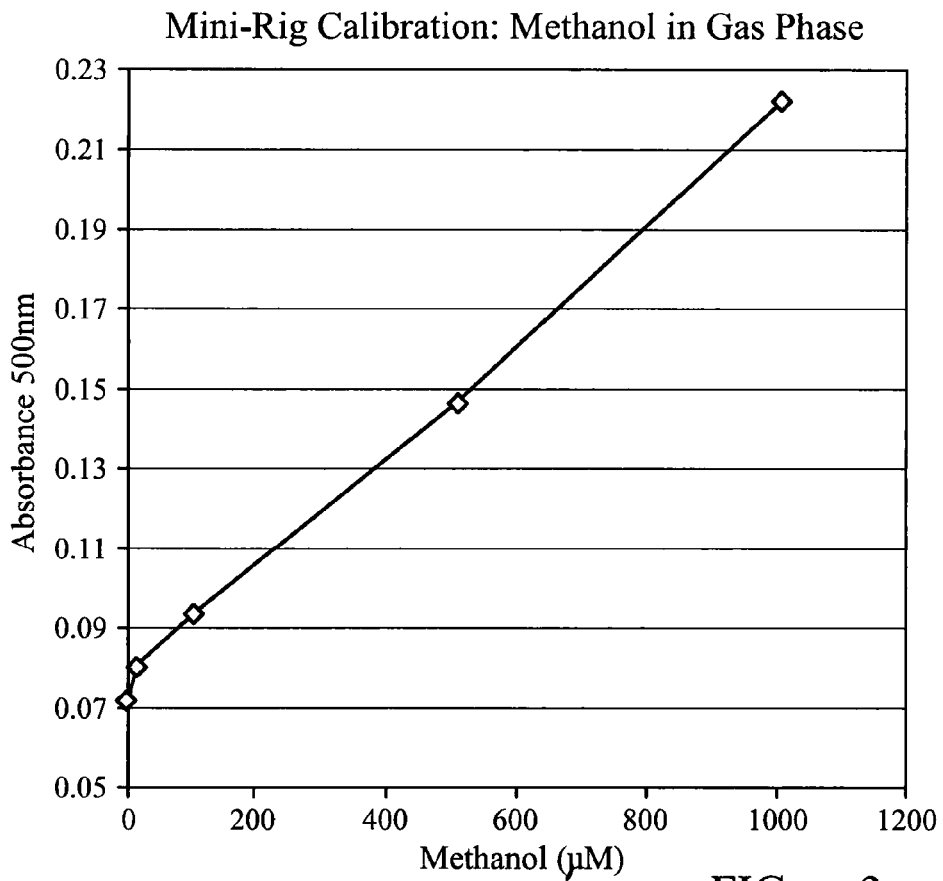
FIG. 3 shows a methanol calibration plot.

Removal of methane from the gas mixture resulted in no colour, whereas addition of methane gave a strong purple colour indicating active bioconversion Colour development was checked against a calibration plot for methanol (FIG. 3 below) and found to give almost 1 mMole of methanol in 20 minutes incubation at room temperature.

| Sample | Absorbance | Methanol (µM) |
|---|---|---|
| Methanol production air and methane | 0.209 | 946 |

Rapid Enzyme Paper Method for Detection of Methanol.

Figure 4:
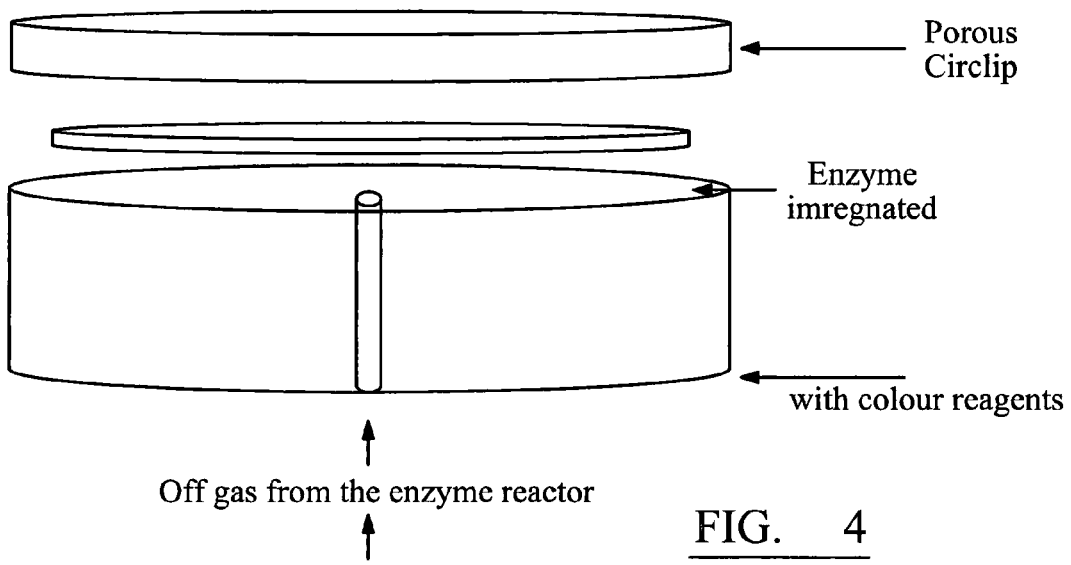
FIG. 4 shows a dry phase methanol detection device.

A visual dry phase test was used. This allowed the detection of methanol on a solid dry phase support, as shown in FIG. 4. FIG. 4 shows an annular support (1) carrying a disc (2) impregnated with enzyme and colour magnets and several by a porous circlip (3).

Analyte containing gas (4) from a reactor (not shown) passes through the diffuser to create a visible colour reaction in the enzyme disc.

Figure 5:
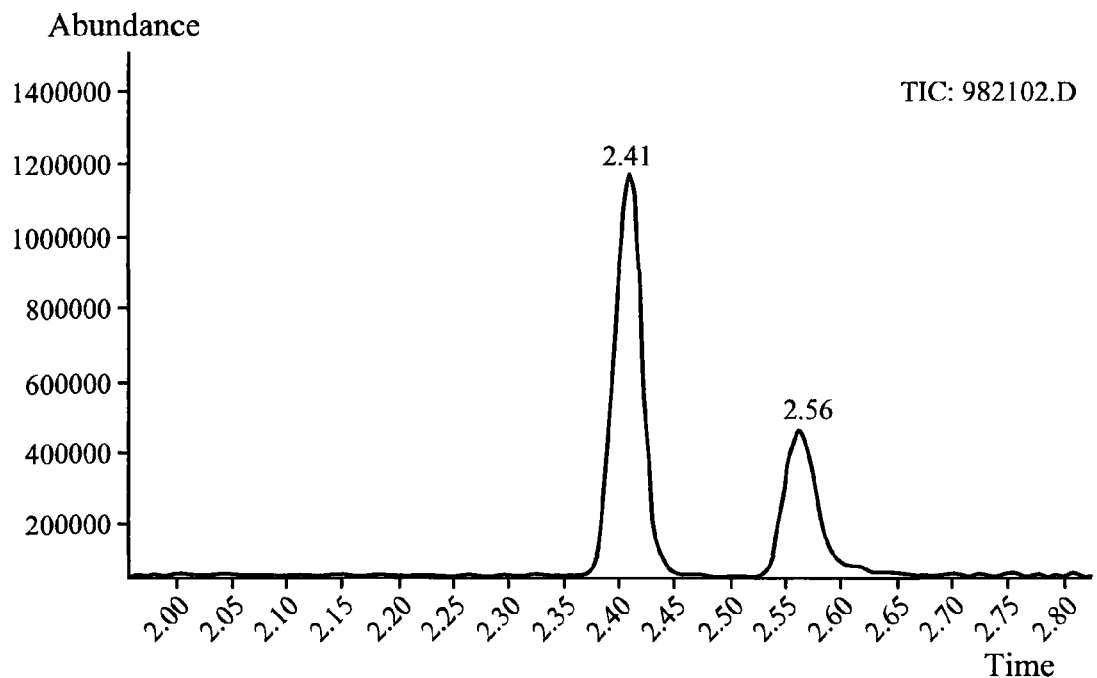
FIG. 5 shows a gas chromatograph for acetone conversion to isopropanol and prenol to prenal.
Figure 5:
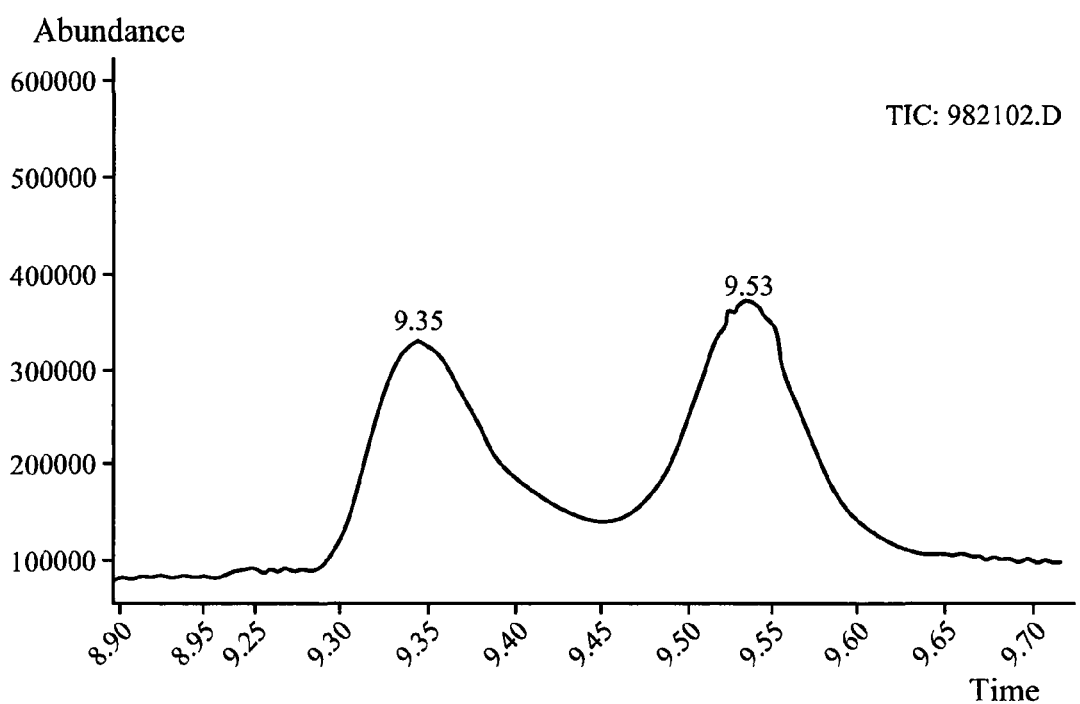

The off gases from the enzyme reactor caused a purple spot in the centre of the enzyme paper when methanol was present. This is not quantitative but as a qualitative test it is very useful to visualise methanol production in a few minutes. This is shown in FIG. 5a The methanol produced was due to MMO activity and not just an artefact or impurities in reagents. With just air and $CO_2$ alone for 1 hour, then testing the off gases with the rapid paper method gave no visual colour, indicating no methanol was present in the off gases. Adding methane into the gas stream and incubating for 1 hour again, then testing with the paper detector gave a strong purple colour in the centre of the detector. Indicating methanol was being produced again from the methane added by the MMO. This is shown in FIG. 5b 2. Alcohol Dehydrogenase Bovine serum albumin (2 g) was added to 10 ml of 50 mM phosphate buffer pH 7.8 and added to 4 g of SI 1410 silica beads. The mixture was dried overnight at 40° C. under reduced pressure and sieved through a 125 micron metal sieve to give free flowing BSA-silica powder. Freeze dried yeast alcohol dehydrogenase (2 g) was added 10 ml of 50 mM phosphate buffer pH 7.8, plus 1 ml of 15 mM NAD in the same buffer and added to 4 g of the pre-prepared BSA-silica beads. The mixture was dried overnight at 40° C. under reduced pressure and sieved through a 125 micron metal sieve to give free flowing ADH-BSA-silica powder.

The ADH-BSA-silica bead preparation (1 to 2 g) was packed into a 1 cm internal diameter tube to give a fixed bed column that was then perfused with gas phase acetone and prenol vapours in air at 4 ml per minute over a period of several hours (usually over 8 hours).

Figure 6:
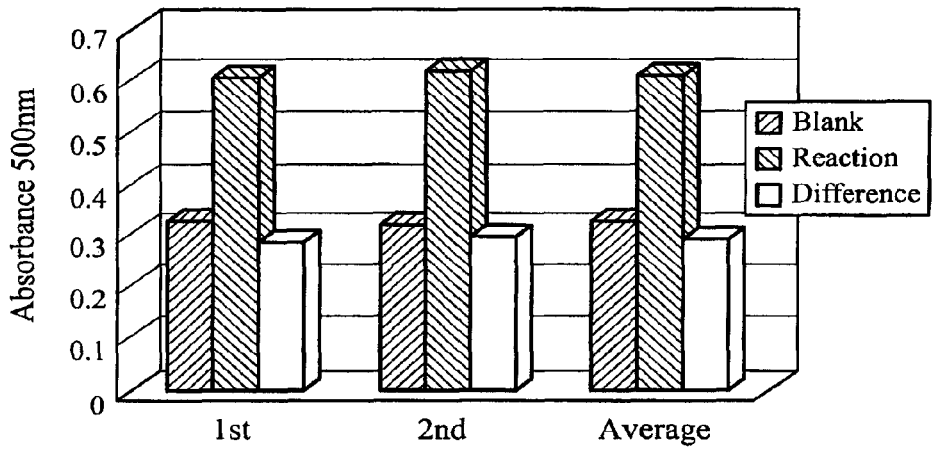
FIG. 6 illustrates conversion of methanol to formic acid.

The appearance of prenal and isopropanol in the exhaust gas stream was observed using a gas chromatography method (GC), indicating enzyme activity was occurring according to FIG. 6.

Further to this method, which is slow to produce product, a fluidised bed was tested. Here 15 g BSA-silica (1 g to 1 g ratio) was added to 15 g of BSA-ADH-silica (400 mg BSA plus 500 mg ADH per gram silica) was added to a 2 inch column reactor and gas phase acetone and prenol vapours in air was introduced at 12 ml per minute to give an air supported fluidised bed of enzyme beads. The reactor produced a 1:1 ratio of isopropanol/acetone for several days indicating enzymatic conversion was taking place continually in the dry phase.

3. Conversion of Methanol to Formic Acid with Concomitant $CO_2$ Sequestration

A preparation of freshly immobilised enzyme beads made with 161 mg ADH, 152 mg FADH and 199 mg FODH added to 9 ml of 50 mM phosphate buffer pH 7.5 plus 1 ml of 15 mM NAD. This was added to 1.032 g BSA coated silica beads and then vacuum dried overnight at 40° C.

The resulting dry powder was then gently ground and passed through a 125 μm sieve to remove any larger aggregates. The large aggregates were re-ground and sieved until the whole volume of the enzyme beads were 125 μm or smaller.

These dry enzyme beads were then fluidised in the gas phase rig using $CO_2$ and methanol was introduced into the flowing stream to start the reaction. The off-gasses were captured in 1.5 ml 10 mM NaOH solution and assayed using an enzymatic formate assay based on the production of a red formazan from the NADH generated by formate dehydrogenase and NAD. This reaction was absolutely specific for formic acid and formate salts. Therefore any colour development is the result of the presence of these entities in solution.

Figure 7:
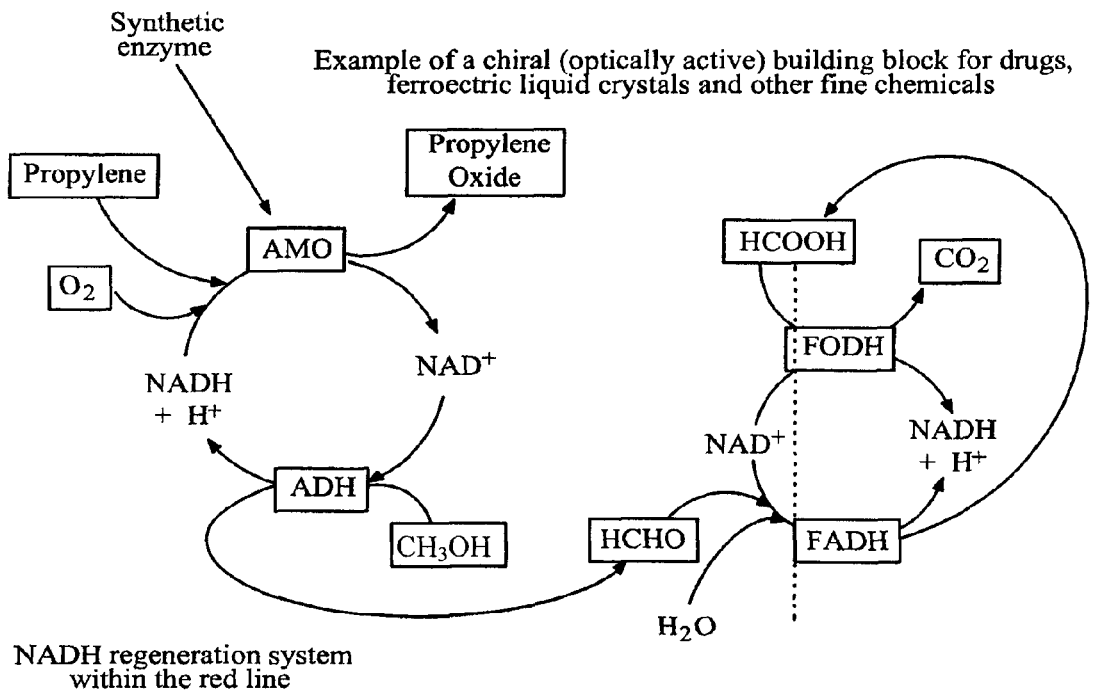
FIG. 7 shows a reaction sequence for alkene mono-oxygenase biocatalysis.

The reaction was run for 2 hours initially and the results are shown in FIG. 7.

The duplicate assays are shown plus the average of the two. In this case 120.4 μMolar formic acid was measured in the 1.5 ml reaction volume, indicating that the three enzyme system of ADH/FADH/FODH has used methanol and $CO_2$ present in the gas phase with the added NAD, enabling cofactor re-cycling to produce formic acid. In all cases the carrier gas ($CO_2$) was humidified with water before it was passed over the three enzyme beads, leading to the likely formation of a water film on the bead surfaces. In real terms at the nanoscale there would be a substantial layer of water present and the NAD would be dissolved in this layer, allowing to cofactor migration between the enzymes and thus cofactor recycling between the three enzymes in this system. This may reflect the natural conditions for enzyme activity, since in cells the water activity is much lower than in vitro experiments, i.e. there is not much liquid water available under normal metabolic conditions. In cells, enzymes do not work in dilute solutions but are present in highly concentrated states.

4. Conversion of Methane to Formic Acid with Concomitant $CO_2$ Sequestration

A preparation of freshly immobilised enzyme beads made with 150 mg ADH, 150 mg FADH and 200 mg FODH added to 8 ml of 50 mM phosphate buffer pH 7.5 plus 1 ml of 15 mM NAD and 1 ml of crude MMO lysate. This was added to 1.0 g BSA coated silica beads and then vacuum dried overnight at 40° C.

The resulting dry powder was gently ground and passed through a 125 μm sieve to remove any larger aggregates. The large aggregates were re-ground and sieved until the whole volume of the enzyme beads were 125 μm or smaller.

The mini-column reactor was constructed as before using between 200-250 mg of enzyme beads in the perfluoroacetate column. Different mixtures of gases were perfused through the beads and the formic acid generated was measured using the specific formate formazan assay described previously.

Using just air and methane generated formic acid from the MMO, ADH and FADH.

Adding $CO_2$ to the gas mixture adds the FODH reaction and an increase in the formic acid produced. This is shown in Table 1 overleaf.

TABLE 1

Generation of Formic Acid from MMO, ADH, FADH and FODH Beads.

| Sample | Time | Average Absorbance | Formic Acid ($\mu M \cdot mg^{-1}$ on beads) |
|---|---|---|---|
| Distilled Water Blank | 0 | 0.2825 | |
| Air/methane/$CO_2$ on BSA coated beads BLANK | | | |
| 1) BSA control - distilled water collection | 30 min | 0.2795 | |
| 2) BSA control - bead extraction | 30 min | 0.3145 | 5.87 |
| Air/methane only MMO/ADH/FADH activity only | | | |
| 3) Gas phase formic collected into 1 ml water | 30 min | 0.3125 | |
| 4) Beads extracted into water | 30 min | 1.3225 | 190.84 |
| 5) Gas phase formic collected into 1 ml water | 30 min | 0.3145 | |
| 6) Beads extracted into water | 30 min | 1.3145 | 192.31 |
| Air/methane/$CO_2$ MMO/ADH/FADH and FODH activity | | | |
| 7) Gas phase formic collected into 1 ml water | 30 min | 0.269 | |
| 8) Beads extracted into water | 30 min | 1.2775 | 366.08 |
| 9) Gas phase formic collected into 1 ml water | 30 min | 0.2675 | |
| 10) Beads extracted into water | 30 min | 1.325 | 364.09 |

In addition to measuring the formate produced, the generation of methanol in the Mini-Column Reactor used above was also measured using both the liquid reagent and the methanol disk method outlined in Example 1.

Figure 8:
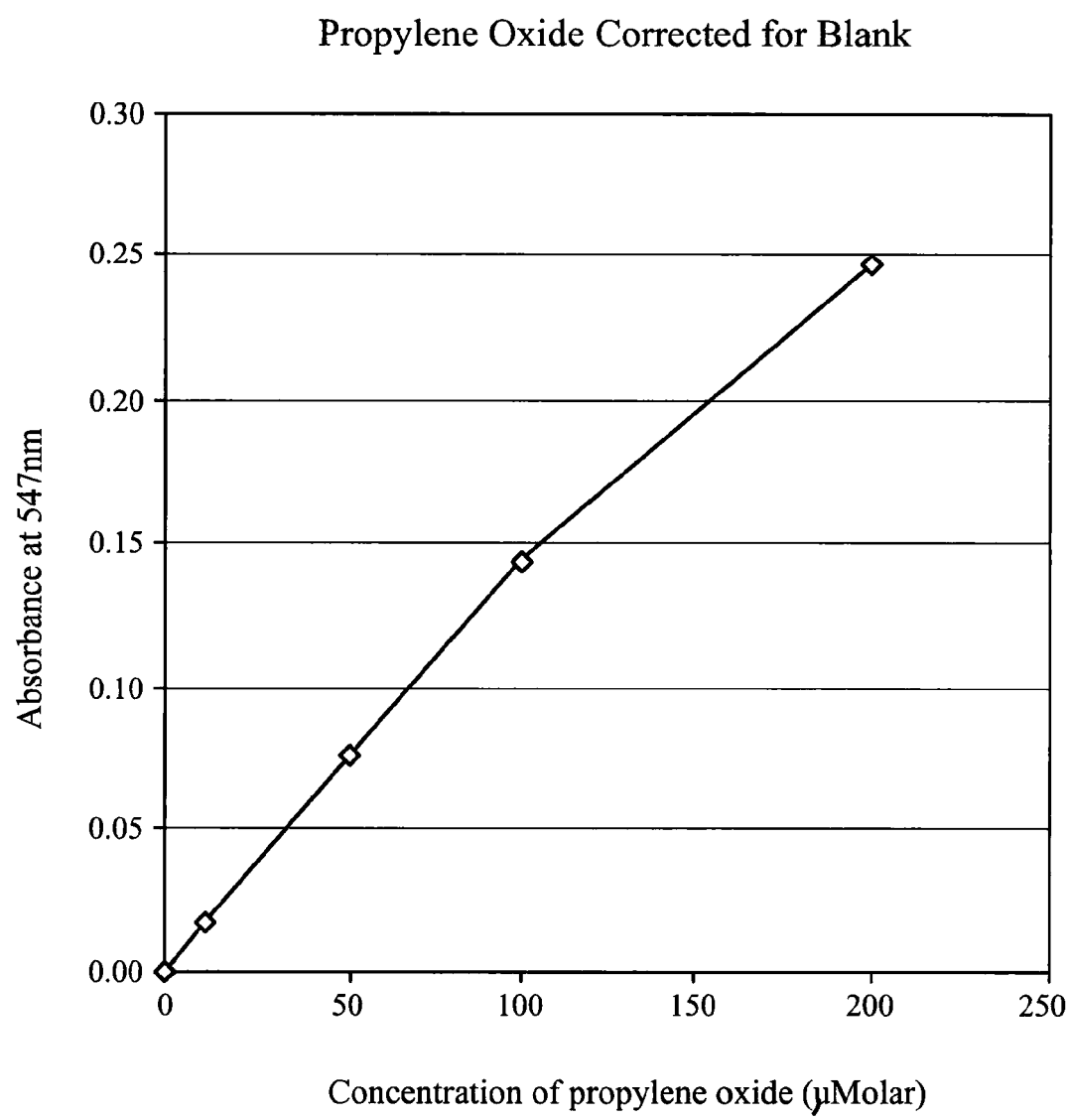
FIG. 8 shows a R-propylene oxide calibration plot.

It is clear from FIG. 8, that methanol was produced by the MMO immobilised onto the BSA coated silica beads, even in the presence of all the other three enzymes (ADH, FADH and FODH).

This was quantified by the liquid methanol reagent as 86.9 μM in 30 minutes. This value will be the amount of methanol in excess of that being used by the ADH and indirectly the other two enzymes, as all four enzymes were immobilised on the BSA silica beads and all were active as evidenced by the results obtained.

This was quantified by the liquid methanol reagent as 86.9 μM in 30 minutes. This value will be the amount of methanol in excess of that being used by the ADH and indirectly the other two enzymes, as all four enzymes were immobilised on the BSA silica beads and all were active as evidenced by the results obtained.

5. R-Propylene Oxide Production Using AMO

AMO cell free extract (500 μl~3 mg enzyme) was added to 500 μl 100 mM MOPS pH 7.2 containing around 10 mg each of ADH.FADH and FODH then thoroughly mixed with around 200 mg silica beads containing pre-dried BSA as an undercoat, then these were dried for 1.5 hours at 40° C. in a vacuum oven over fresh silica gel. No extra NAD or NADH was added to this first dried enzymes mixture. The dried beads/enzymes were ground to a fine powder in an agate mortar and pestle, then packed into 2 mm ID tubing (around 170 mg per tube) and assayed in the Climostat mini-rig system at room temperature using a mixture of air, methanol vapour and propylene.

Propylene oxide generation was followed using a simple colorimetric assay system using the reaction N-benzyl pyridine with the propylene oxide, which gives a bright purple colour when extracted into an organic solvent layer (FIG. 8 on page 17).

| AMO preparation | μg in 30 minutes | μg in 90 minutes |
|---|---|---|
| AMO 1 | — | 11.62 |
| AMO 2 | 6.38 | 11.92 |

The invention claimed is:

1. A method of enzyme conversion, comprising:
   immobilizing an enzyme composition on porous inorganic beads forming a support material;
   drying the support material and enzyme composition to form a solid phase immobilized enzyme system with a water content of between 0.05% w/v to 5% w/v;
   contacting the enzyme system with one or more reagents in the gas phase;
   allowing the enzyme system with a water content of between 0.05% w/v to 5% w/v to convert the one or more reagent in gas phase to one or more product;
   wherein the enzyme composition is selected from the group consisting of a first enzyme plus a second enzyme or multiple enzymes; and a co-factor convertable between first and second states;
   wherein the co-factor in the first state promotes reaction of the first enzyme with a first gas phase reagent; and
   wherein the co-factor in the second state promotes reaction of the second enzyme with a second gas phase reagent.

2. A method as claimed in claim 1, wherein the co-factor is oxidized/reduced nicotinamide adenine dinucleotide (NAD/NADH).

3. A method as claimed in claim 1, wherein the co-factor is oxidized/reduced flavin mononucleotide (FMN/FMNH).

4. A method as claimed in claim 1, wherein the co-factor is oxidized/reduced flavin adenine dinucleotide (FAD/FADH).

5. A method as claimed in claim 1, wherein the co-factor is oxidized/reduced pyrroloquinoline quinone (PQQ/PQQH$_2$).

6. A method as claimed in claim 1, wherein the support material is a particulate support material fluidised by passage of the gas phase reagent.

7. A method as claimed in claim 1, wherein the first enzyme is a monooxygenase enzyme.

8. A method as claimed in claim 7, wherein the monooxygenase enzyme is selected from the group consisting of methane monooxygenase and alkene monooxygenase.

9. A method as claimed in claim 7, wherein the second enzyme or multiple enzymes is alcohol dehydrogenase, formaldehyde dehydrogenase and formate dehydrogenase.

10. A method as claimed in claim 1, wherein the second enzyme or multiple enzymes is selected from the group consisting of alcohol dehydrogenase, formaldehyde dehydrogenase, formate dehydrogenase, and a combination thereof.

11. A method as claimed in claim 1, wherein the one or more reagents comprises methane and the product comprises methanol.

12. A method as claimed in claim 1, wherein the one or more reagents comprises methanol and the product comprises formic acid.

13. A method as claimed in claim 1, wherein the co-factor oscillates between first and second states with multiple enzymes.

14. An enzymic conversion system, comprising:
   an enzyme composition comprising a first enzyme, a second enzyme and a co-factor, which may be converted between first and second states, immobilized on a support material;
   wherein the co-factor in the first state promotes reaction of the first enzyme with a gas phase reagent;
   wherein the co-factor in the second state promotes reaction of the second enzyme with a gas phase reagent;
   wherein the support material is composed of porous inorganic beads; and
   wherein the enzymic conversion system has a water content of between 0.05% w/v to 5% w/v.

15. A sensor comprising a system as claimed in claim 14.

* * * * *